US012715830B2

(12) United States Patent
Galan-Sanchez et al.

(10) Patent No.: US 12,715,830 B2
(45) Date of Patent: Aug. 25, 2026

(54) PROCESS CONFIGURATION FOR A SINGLE PHENOL PURIFICATION TRAIN FOR PRODUCTION OF PHENOL AND BISPHENOL-A IN AN INTEGRATED PROCESS

(71) Applicant: SABIC Global Technologies B.V., Bergen op Zoom (NL)

(72) Inventors: Lara Galan-Sanchez, Eindhoven (NL); Kae Shin Wong, Maasmechelen (BE); Kadek Sumpena, Nederweert (NL); Martino Trabuio, Eindhoven (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 581 days.

(21) Appl. No.: 18/039,745

(22) PCT Filed: Dec. 1, 2021

(86) PCT No.: PCT/IB2021/061177

§ 371 (c)(1),
(2) Date: Jun. 1, 2023

(87) PCT Pub. No.: WO2022/118213

PCT Pub. Date: Jun. 9, 2022

(65) Prior Publication Data

US 2024/0025830 A1 Jan. 25, 2024

Related U.S. Application Data

(60) Provisional application No. 63/120,139, filed on Dec. 1, 2020.

(51) Int. Cl.

| | |
|---|---|
| ***C07C 37/80*** | (2006.01) |
| ***C07C 37/00*** | (2006.01) |
| ***C07C 37/68*** | (2006.01) |
| ***C07C 37/84*** | (2006.01) |

(52) U.S. Cl.

CPC ............ *C07C 37/80* (2013.01); *C07C 37/005* (2013.01); *C07C 37/685* (2013.01)

(58) Field of Classification Search

CPC ........ C07C 37/80; C07C 37/84; C07C 37/005
See application file for complete search history.

(56) References Cited

U.S. PATENT DOCUMENTS

| | | | |
|---|---|---|---|
| 10,246,391 | B2 | 4/2019 | Nelson et al. |
| 2005/0222467 | A1 | 10/2005 | Kodama et al. |

FOREIGN PATENT DOCUMENTS

| | | | |
|---|---|---|---|
| JP | 3775832 | B2 | 4/1997 |
| WO | 2012170327 | A1 | 12/2012 |
| WO | 2014070742 | A1 | 5/2014 |

OTHER PUBLICATIONS

International Search Report for International Application No. PCT/IB2021/061177; International Filing Date Dec. 1, 2021; Date of Mailing Feb. 9, 2022; 3 pages.
Written Opinion for International Application No. PCT/IB2021/061177; International Filing Date Dec. 1, 2021; Date of Mailing Feb. 9, 2022; 6 pages.
Office Action for the corresponding application in United Arab Emirates, application No. P6001289/2023, Date of Mailing: Dec. 23, 2024; 8 pages (English translation).

*Primary Examiner* — Sikarl A Witherspoon
(74) *Attorney, Agent, or Firm* — CANTOR COLBURN LLP

(57) ABSTRACT

A method for purifying phenol can include contacting a first stream containing phenol with a second stream containing wastewater from a bisphenol-A (BPA) production process to form a third stream, distilling the third stream to form a fourth stream containing phenol and water, contacting the fourth stream with a fifth stream containing mother liquor from a BPA crystallization unit of the BPA production process to form a sixth stream, and distilling the sixth stream to form a products stream containing phenol.

19 Claims, 5 Drawing Sheets

PROCESS CONFIGURATION FOR A SINGLE PHENOL PURIFICATION TRAIN FOR PRODUCTION OF PHENOL AND BISPHENOL-A IN AN INTEGRATED PROCESS

CROSS-REFERENCE TO RELATED APPLICATIONS

This application is a National Stage application of PCT/IB2021/061177, filed Dec. 1, 2021, which claims the benefit of priority to U.S. Provisional Patent Application No. 63/120,139, filed Dec. 1, 2020, both of which are hereby incorporated by reference in their entireties.

FIELD OF INVENTION

The present invention generally relates to a process for purifying phenol.

BACKGROUND OF THE INVENTION

Phenol is an important commodity chemical. For example, phenol can be used to produce various phenolic derivatives (e.g., bisphenol-A (BPA), butylated hydroxytoluene, 4-nonyl phenol, o-phenyl phenol, picric acid, phenolphthalein, xylenol, and the like). These phenolic derivatives can have a variety of downstream uses (e.g., precursor for plastic materials, additives used in plastic materials, laboratory reagents, medical uses, agricultural uses, etc.). Phenol can be prepared by a cumene oxidation process.

As noted above, BPA is oftentimes used as a precursor for various plastic materials (e.g. polycarbonates, polysulfones, and epoxy resins etc.). These plastic materials have multiple industrial uses and can be used to produce various consumer products. BPA can be produced by a reaction between acetone and phenol. Unreacted phenol in the BPA production process is typically purified and reused in the BPA production process.

Phenol purification in the phenol production process, and unreacted phenol purification in the BPA production process, both involve multiple steps and require relatively high capital expenditure and energy. Attempts have been made to optimize the phenol purification process. For example, U.S. Pat. No. 10,246,391B2 describes a process for recovering phenol from a BPA production facility where a purge stream containing 60 to 90 wt. %, of phenol is added to a phenol purification section of a phenol production facility. Implementation of this purge stream to a phenol production facility can be complicated and time consuming.

BRIEF SUMMARY OF THE INVENTION

A discovery has been made that provides a solution to at least some of the problems associated with purification of phenol. In one aspect, a solution can include integrating the phenol purification section of a phenol production process with a BPA production process. For example, the solution can include i) using phenolic water from the BPA production process as an azeotropic separation agent in a hydrocarbon removal column used for separation of phenols produced in the phenol production process, and ii) drying wet phenol produced by the hydrocarbon removal column to form high purity phenol. By comparison, conventional phenol production processes typically use clean water as the azeotropic separation agent. In one aspect of the present invention, it was discovered that use of phenolic water from the BPA production process in the phenolic purification process can optimize resource utilization of the processes and reduce complexity of the processes (e.g., (1) use of phenolic water in the hydrocarbon removal column can reduce clean water usage in the column and/or (2) a wet phenol from the hydrocarbon removal column and a wet phenol from the BPA production process can be dried together in a same phenol drying column). Further, and as illustrated in a non-limiting manner in the Examples section, a higher phenol recovery and/or purity can be obtained with the processes of the present invention when compared with conventional phenol production processes.

One aspect of the present invention is directed to a method for purifying phenol. The method can include any one of, any combinations of, or all of steps (a), (b), (c), and (d). In step (a) a first stream containing phenol can be contacted with a second stream containing wastewater from a bisphenol-A (BPA) production process to form a third stream. In step (b) the third stream can be distilled to form a fourth stream containing phenol and water. In step (c) the fourth stream can be contacted with a fifth stream containing mother liquor from a BPA crystallization unit of the BPA production process to form a sixth stream. In step (d) the sixth stream can be distilled to form a products stream containing phenol. Wt. % of phenol in the products stream can be higher than that in the first stream. The first stream can contain 95 wt. % or higher phenol, such as 95 wt. % to 98 wt. % of phenol. In some aspects, the first stream can be obtained from a cumene oxidation based phenol production process. An effluent stream, from the cumene oxidation based phenol production process, containing 60 wt. % to 95 wt. % of phenol can be separated in a crude phenol column to form the first stream. In certain aspects, the effluent stream can be distilled in the crude phenol column at a temperature 120° C. to 180° C. and/or a pressure 0.3 bar to 0.6 bar, to purify phenol and to obtain the first stream. In some aspects, the first stream can further contain unreacted reactants, byproducts and/or side products from the cumene based oxidation process, such as carbonyls, 2-methyl benzofuran (MBF) and/or other non-phenol hydrocarbons such as cumene, alpha methyl styrene (AMS), AMS dimers, dimethyl benzyl alcohol (DMBA), para cumyl phenol (PCP), alkyl benzenes, and/or dicumylperoxide (DCP). In certain aspects, the first stream can contain 0.1 wt. % to 1.5 wt. % of carbonyls, and 0.1 wt. % to 1 wt. % of 2-MBF. The wastewater from the BPA production process can contain phenolic water, and the second stream can contain the phenolic water. In some aspects, the second stream can contain 0.1 wt. % to 3 wt. % of phenol and 97 wt. % to 99.9 wt. % of water. The third stream can be distilled and separated by extractive distillation using water as an azeotropic separation agent (e.g. separation solvent) and phenol can get hydroextracted to form the fourth stream containing wet phenol (e.g. phenol and water). The third stream can be distilled (e.g., by extractive distillation) in a hydrocarbon removal column. In certain aspects, the distillation conditions of the third stream in the hydrocarbon removal column can include a temperature 190° C. to 230° C. and/or a pressure 1 bar to 3 bar. The distillation of the third stream can separate at least a portion of the carbonyls, 2-MBF and/or the other non-phenol hydrocarbons from phenol. The fourth stream can be formed as a bottom distillate from the hydrocarbon removal column. A seventh stream containing carbonyls and 2-MBF can be formed as a top distillate from the hydrocarbon removal column. In certain aspects, an acid such as water soluble acid, can be added to the hydrocarbon removal column, e.g., via the third stream and/or separately.

The acid can assist in the hydroextraction operation occurring in the column and facilitate separation of phenol from the carbonyls, 2-MBF and/or the other non-phenol hydrocarbons. In some aspects, the acid can be sulfonic acid. In some aspects, the fourth stream can be further processed to remove at least a portion of residual carbonyls, 2-MBF and/or the other non-phenol hydrocarbons from the fourth stream and produce a processed fourth stream, and the processed fourth stream can be contacted with the fifth stream to form the sixth stream. The fourth stream can be processed by extractive distillation (e.g., hydroextractive distillation) using water as an azeotropic separation agent. In some aspects, the extractive distillation conditions of the fourth stream can include a temperature of 70° C. to 220° C. and/or a pressure of 1 bar to 4 bar. The fifth stream can be obtained from the BPA crystallization unit by i) vacuum filtering mother liquor from the BPA crystallization unit to obtain a vacuum filtered stream containing phenol, BPA and water, and/or ii) separating the vacuum filtered stream in a water stripper column to obtain the fifth stream as a top distillate from the water stripper column. In some aspects, the fifth stream can contain 40 wt. % to 58 wt. % of phenol and 35 wt. % to 55 wt. % of water. In some aspects, the second stream and the fifth stream can be obtained from the same BPA production process. In some aspects, the second stream and the fifth stream can be obtained from separate BPA production processes. The sixth stream can be distilled in a phenol finishing and drying column. The sixth stream can be distilled to separate water from phenol, and form the products stream comprising phenol. The sixth stream can be distilled at the phenol drying and finishing column at a temperature 180° C. to 210° C. and/or 0.5 bar to 2 bar. In some aspects, an eight stream containing phenolic water from the BPA production process can be fed to the phenol drying and finishing column. The eight stream can be fed to the phenol drying and finishing column separately, with the fourth stream, with the processed fourth stream, and/or with the fifth stream. In some aspects, the eight stream can contain 0.1 wt. % to 3 wt. % of phenol and 97 wt. % to 99.9 wt. % of water. In some aspects, the eight stream and the second stream can have same or similar composition, and/or can be obtained from same or similar source/unit in the BPA production process. Without wishing to be bound by theory it is believed that adding phenolic water to the drying and finishing column can concentrate phenol at the top of the column, and may increase total phenol recovery. In certain aspects, the products stream can contain greater than 98 wt. %, preferably 99 wt. % to 99.998 wt. %, of phenol. In some aspects, the products stream can contain less than 0.05 wt. % of carbonyls and less than 0.01 wt. % of 2-MBF. Phenols from the products stream can be stored, recycled to BPA production process to form BPA, and/or used in other process(es).

In one aspect of the present invention, there is also disclosed a system, which can be used with the processes of the present invention. The system can include a hydrocarbon removal unit, and a phenol drying and finishing unit. The hydrocarbon removal unit can be configured to receive a first stream containing phenol, and a second stream containing wastewater from a bisphenol-A (BPA) production process. The first stream, and second stream can be contacted to form a third stream, and the hydrocarbon removal unit can be configured to form a fourth stream containing phenol and water, by distillation, e.g. extractive distillation, of the third stream. The hydrocarbon removal unit can contain a hydrocarbon removal column and the third stream can be distilled e.g. via extractive distillation, to form the fourth stream in the hydrocarbon removal column. The phenol drying and finishing unit can be configured to receive the fourth stream, and a fifth stream containing mother liquor from a BPA crystallization unit of the BPA production process. The fourth stream and fifth stream can be contacted to form a sixth stream, and the phenol drying and finishing unit can be configured to form a products stream containing phenol, by distillation of the sixth stream. The phenol drying and finishing unit can contain a phenol drying and finishing column, and the sixth stream can be distilled to form the products stream in the phenol drying and finishing column. In certain aspects, the system can further include a crude phenol treatment unit. The crude phenol treatment unit can be configured to receive an effluent stream from a phenol production process, such as a cumene oxidation based phenol production process, and form the first stream by distillation the effluent stream. The crude phenol treatment unit can contain a crude phenol column and the effluent stream can be distilled to form the first stream in the crude phenol column. In certain aspects, the system can further contain a phenol treatment unit. The phenol treatment unit can be configured to receive the fourth stream and remove at least a portion of non-phenol hydrocarbons from the fourth stream and produce a processed fourth stream. The processed fourth stream can be contacted with the fifth stream to form the sixth stream. The streams, e.g. effluent, first, second, third, fourth, processed fourth, fifth, sixth, and products streams, can be configured and have composition as described above, e.g. for the method for purifying phenol. The units, e.g. crude phenol treatment unit, hydrocarbon removal unit, phenol treatment unit, and phenol drying and finishing unit, can be configured and/or operated as described above, e.g. for the method for purifying phenol.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %," or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The phrase "and/or" can include "and" or "or." To illustrate, A, B, and/or C can include: A alone, B alone, C alone, a combination of A and B, a combination of A and C, a combination of B and C, or a combination of A, B, and C.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification. In one non-limiting aspect, and with respect to the phrase "consist (consisting) essentially of," a basic and novel characteristic of the present invention can include increased production and/or purity of phenol.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

DETAILED DESCRIPTION OF THE INVENTION

A discovery has been made that provides a solution to at least some of the problems associated with purification of phenol. One aspect of the present invention can include integrating the phenol purification methods of a phenol production process with a BPA production process. As shown in a non-limiting manner in the Examples section, higher phenol recovery than a conventional phenol purification method can be obtained by the methods of the present invention while using relatively lesser resource and energy. In one aspect, phenolic water from the BPA production process can be used as an azeotropic separation agent in a hydrocarbon removal column used for separation of phenol in the phenol production process. Use of phenolic water in the hydrocarbon removal column can reduce clean water usage in the column. Further, a wet phenol from the hydrocarbon removal column and a wet phenol from the BPA production process can be dried together in a same phenol drying column, optimizing resource utilization and reducing complexity of the methods.

These and other non-limiting aspects of the present invention are discussed in further detail in the following sections with reference to the figures. The units shown in the figures can include one or more heating and/or cooling devices (e.g., insulation, electrical heaters, jacketed heat exchangers in the wall) or controllers (e.g., computers, flow valves, automated values, etc.) that can be used to control temperatures and pressures of the processes. While only one unit is usually shown, it should be understood that multiple units can be housed in one unit.

Figures 1A, 1B:
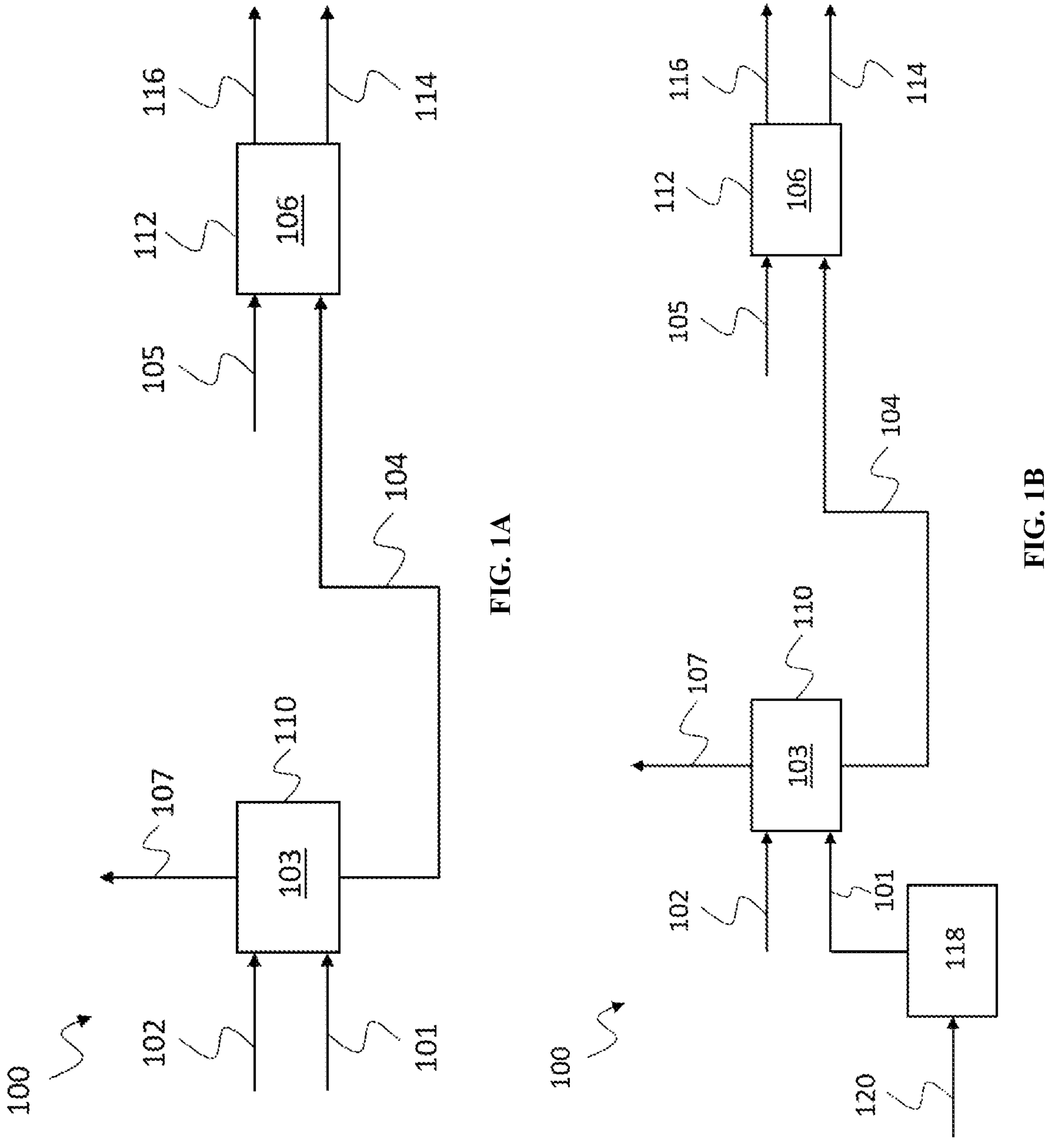
FIGS. 1A and 1B are schematics of an example of the present invention to purify phenol.

Referring to FIGS. 1A and 1B, systems and methods for purifying phenol according to one example of the present invention is described. The system 100 can include a hydrocarbon removal unit 110 and phenol drying and finishing unit 112. A first stream 101 containing phenol, and a second stream 102 containing wastewater from a bisphenol-A (BPA) production process can be fed to the hydrocarbon removal unit 110. In the hydrocarbon removal unit 110, the first stream 101 and the second stream 102 can be contacted to form a third stream 103. The first stream 101 and the second stream 102 can be fed to the hydrocarbon removal unit 110 separately and the stream 103 can be formed in the hydrocarbon removal unit 110, or the streams 101, 102 can be combined prior to feeding to the hydrocarbon removal unit 110 forming the stream 103 and the stream 103 can be fed to the hydrocarbon removal unit 110 (not shown). In the hydrocarbon removal unit 110 the third stream 103 can be separated to form a fourth stream 104 containing phenol and water, and a seventh stream 107. The fourth stream 104 containing wet phenol, e.g. phenol and water, from the hydrocarbon removal unit 110 can be fed to the phenol drying and finishing unit 112. A fifth stream 105 containing mother liquor from a BPA crystallization unit of the BPA production process can be fed to the phenol drying and finishing unit 112. The streams 102 and 105 can be obtained from the same or different BPA production process. In some aspects, the streams 102 and 105 can be obtained from the same BPA production process. The streams 104 and 105 can be contacted in the unit 112 to form a sixth stream 106. The fourth stream 104 and the fifth stream 105 can be fed to the unit 112 separately and the sixth stream 106 can be formed in the unit 112, or the streams 104, 105 can be combined prior to feeding to the unit 112 forming the stream 106 and the stream 106 can be fed to the unit 112 (not shown). In the phenol drying and finishing unit 112 the sixth stream 106 can be separated to form a products stream 114 containing phenol and a stream 116 containing water. In some aspects, the first stream 101 can be obtained from a phenol production process. In some aspects, the phenol production process can be a cumene oxidation based process. Referring to FIG. 1B, in certain aspects, the system 100 can further include a crude phenol treatment unit 118. An stream 120 from the phenol production process, such as cumene oxidation based process, containing phenol can be fed to the crude phenol treatment unit 118. The stream 120 can further contain unreacted reactants, side products and/or by products from the phenol production process, such as carbonyls, 2-methyl benzofuran (MBF) and/or other non-phenol hydrocarbons such as cumene, alpha methyl styrene (AMS), AMS dimers, dimethyl benzyl alcohol (DMBA), para cumyl phenol (PCP), alkyl benzenes, and/or dicumylperoxide (DCP). In the crude phenol unit 118, the stream 120 can be separated to form the first stream 101.

Figure 2A:
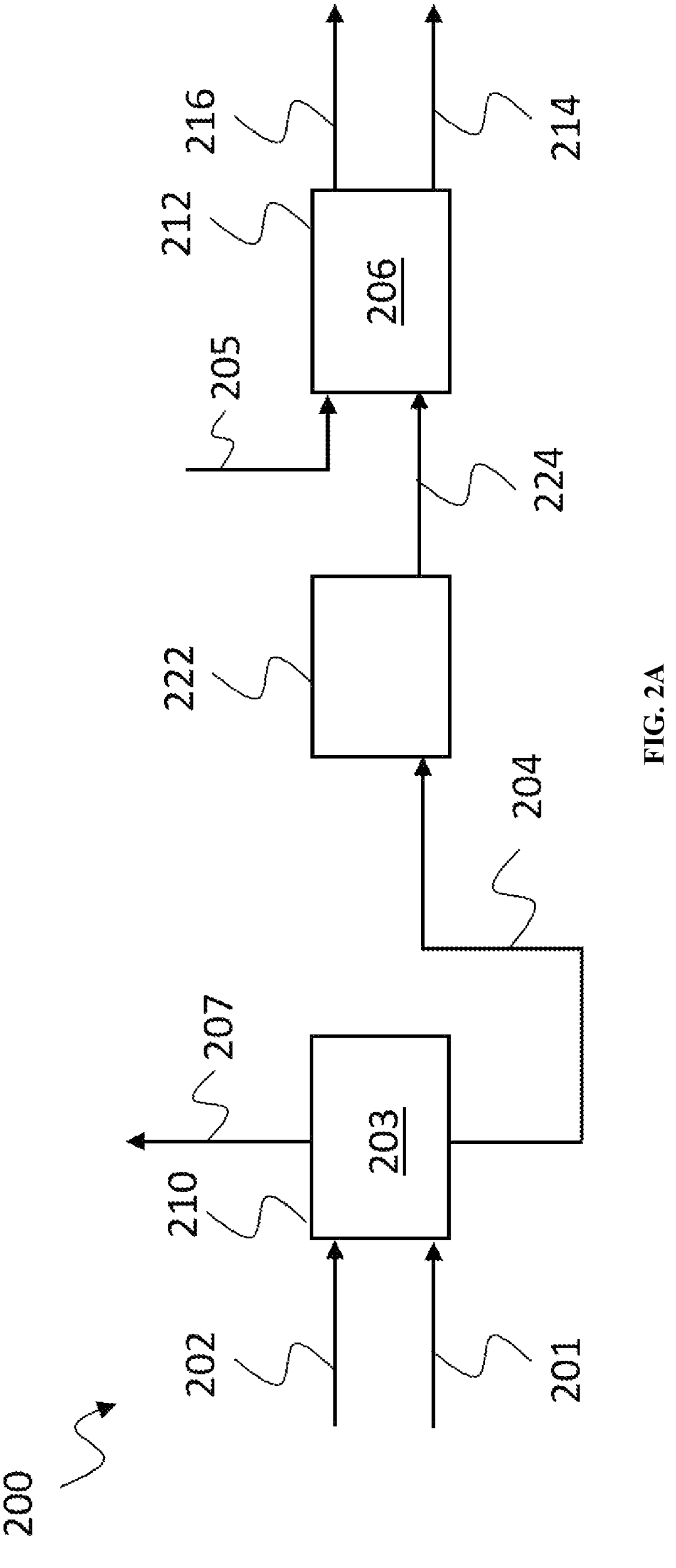
FIGS. 2A and 2B are schematics of a second example of the present invention to purify phenol.
Figure 2B:
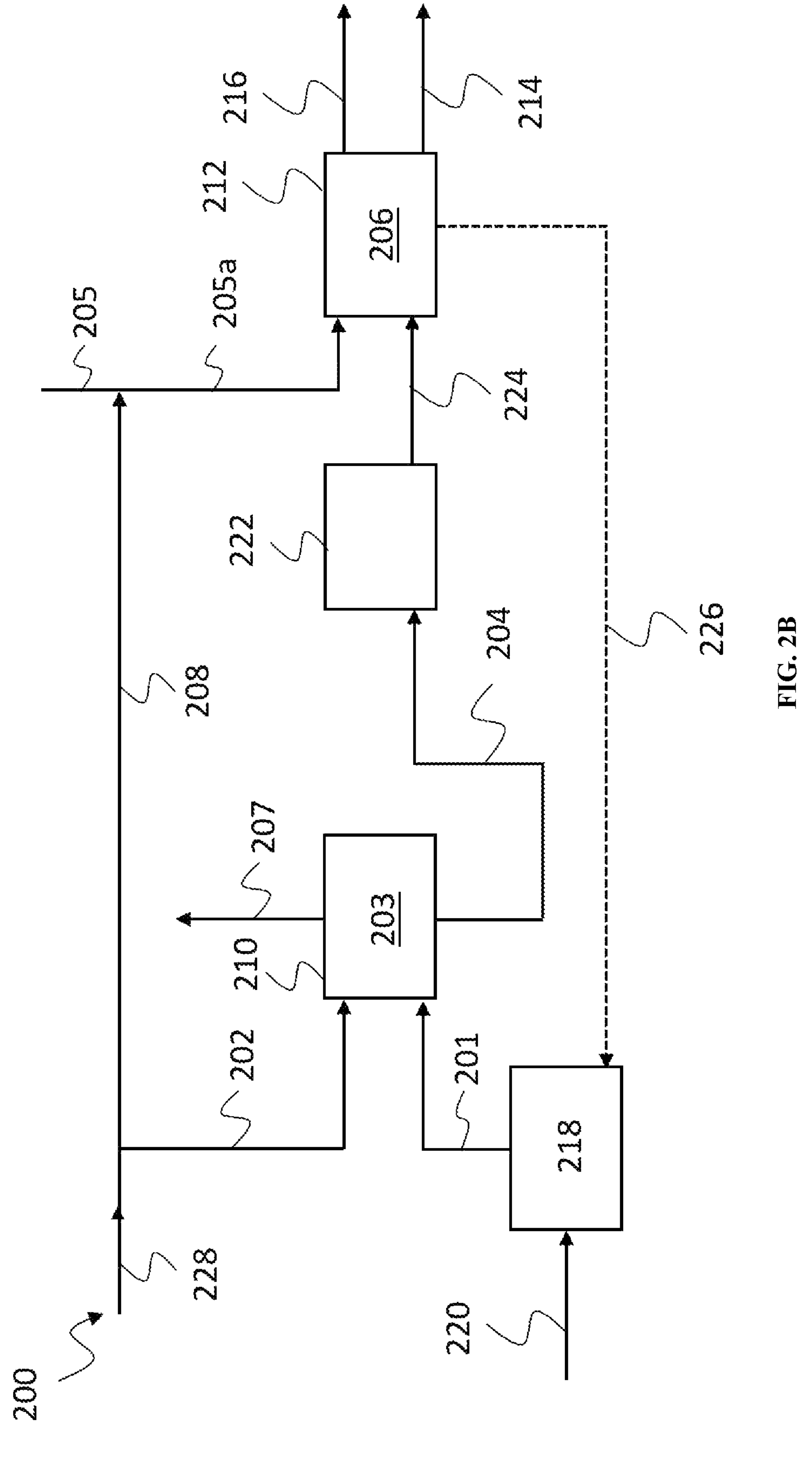

Referring to FIGS. 2A and 2B, systems and methods for purifying phenol according to a second example of the present invention is described. The system 200 can include a hydrocarbon removal unit 210, a phenol treatment unit 222, and a phenol drying and finishing unit 212. A first stream 201 containing phenol and a second stream 202 containing wastewater from a bisphenol-A (BPA) production process can be fed to the hydrocarbon removal unit 210. In the hydrocarbon removal unit 210, the first stream 201 and the second stream 202 can be contacted to form a third stream 203. The first stream 201 and the second stream 202 can be fed to the hydrocarbon removal unit 210 separately and the stream 203 can be formed in the hydrocarbon removal unit 210, or the streams 201, 202 can be combined prior to feeding to the hydrocarbon removal unit 210 forming the stream 203 and the stream 203 can be fed to the hydrocarbon removal unit 210 (not shown). In the hydrocarbon removal unit 210, the third stream 203 can be separated to form a fourth stream 204 containing phenol and water, and a seventh stream 207. The fourth stream 204 containing wet phenol, e.g., phenol and water, from the hydrocarbon removal unit 210 can be fed to the phenol treatment unit 222. In the phenol treatment unit 222, the fourth stream can be processed to form a processed fourth stream 224 containing phenol and water. The stream 224 from the phenol treatment unit 222 can be fed to the phenol drying and finishing unit 212. A fifth stream 205 containing mother liquor from a BPA crystallization unit of the BPA production process can be fed to the phenol drying and finishing unit 212. The streams 202 and 205 can be obtained from the same or different BPA production process. In some aspects, the streams 202 and 205 can be obtained from the same BPA production process. The streams 224 and 205 can be contacted in the unit 212 to form a sixth stream 206. The streams 224 and 205 can be fed to the unit 212 separately and the stream 206 can be formed in the unit 212, or the streams 224 and 205 can be combined prior to feeding to the unit 212 forming the stream 206 and the stream 206 can be fed to the unit 212 (not shown). In the phenol drying and finishing unit 212, the sixth stream 206 can be separated to form a products stream 214 containing phenol and a stream 216 containing water. In some aspects, the first stream 201 can be obtained from a phenol production process, such as cumene oxidation based process. Referring to FIG. 2B in certain aspects, the system 200 can further include a crude phenol treatment unit 218. A stream 220 from the phenol production process containing phenol can be fed to the crude phenol treatment unit 218. The stream 220 can further contain unreacted reactants, side products and/or by products from the phenol production process, such as carbonyls, 2-MBF and/or other non-phenol hydrocarbons such as cumene, AMS, AMS dimers, DMBA, PCP, alkyl benzenes, and/or DCP. In the crude phenol unit 218, the stream 220 can be separated to form the first stream 201. In certain aspects, an eight stream 208 containing wastewater from the BPA production process can be fed to the phenol drying and finishing unit 212. The eight stream 208 can be fed to the unit 212 separately (not shown), or can be mixed with streams 205 and/or stream 224 (not shown) and fed to the unit 212. In some aspects, the eight stream 208 and the fifth stream 205 can be combined to form a stream 205*a* and the stream 205*a* can be fed to the unit 212. The streams 202 and 208 can be obtained from wastewater stream 228 containing phenolic water of the BPA production process. In some aspects, a heavies stream 226 can be separated from the sixth stream 206 in the phenol drying and finishing unit 212. Optionally, the heavies stream 226 can be recycled to the crude phenol unit 218. The heavies stream can contain heavies such as tars, cresols, 2MBF, DMBA, AMS dimers or any combinations thereof.

In the hydrocarbon removal unit 110, 210 phenol can be separated from non-phenol hydrocarbons, such as carbonyls, 2-MBF, and/or others (e.g. cumene, AMS, AMS dimers, DMBA, PCP, alkyl benzenes, and/or DCP) through hydro-extraction. The hydrocarbon removal unit 110, 210 can include a hydrocarbon removal column. In the hydrocarbon removal column the third stream 103, 203 can be distilled by extractive distillation (e.g. hydroextraction) using water as azeotropic separation agent. Water from the second stream can function as the azeotropic separation agent (e.g., separating solvent) and facilitate the separation of phenol from the non-phenol hydrocarbons. In certain aspects, an acid can be added to the hydrocarbon removal column to facilitate the hydroextraction process. The acid can be a water soluble strong acid, such as sulfonic acid. In some aspects, the extractive distillation conditions in the hydrocarbon removal column can include a temperature of 190° C. to 230° C., or at least any one of, equal to any one of, or between any two of 190, 195, 200, 205, 210, 215, 220, 225 and 230° C., and/or a pressure of 1 bar to 3 bar, or at least any one of, equal to any one of, or between any two of 1, 1.2, 1.4, 1.6, 1.8, 2, 2.2, 2.4, 2.6, 2.8, and 3 bar. From the hydrocarbon removal unit 110, 210, phenol and water can get separated in to the fourth stream 104, 204 and non-phenols hydrocarbons can get separated in to the seventh stream 107, 207. In some aspects, the fourth stream 104, 204 can be obtained from the bottom, and the seventh stream 107, 207 can be obtained from the top of the hydrocarbon removal column. In some aspects, a side draw purge stream containing organic acids (e.g., acetic acid) close to the bottom of the hydrocarbon removal column can be removed (not shown) during the distillation of the third stream.

In the phenol finishing and drying unit 112, 212 phenol can be separated from water through distillation. The phenol finishing and drying unit 112, 212 can include a phenol finishing and drying column. In the phenol finishing and drying column the sixth stream 106, 206 can be distilled to separate phenol from water. In some aspects, the distillation conditions in the phenol finishing and drying column can include a temperature of 180° C. to 210° C., or at least any one of, equal to any one of, or between any two of 180, 185, 190, 195, 200, 205, and 210° C., and/or a pressure of 0.5 bar to 2 bar, or at least any one of, equal to any one of, or between any two of 0.5, 0.6, 0.8, 1, 1.2, 1.4, 1.6, 1.8, and 2 bar. From the phenol finishing and drying unit 112, 212, phenol can get separated in to the products stream 114, 214 and water can get separated in to the stream 116, 216. In some aspects, the stream 116, 216 can be purged from the top of the phenol finishing and drying column. In some aspects, the stream 114, 214 can be obtained from a top section of the phenol finishing and drying column. In some aspects, the heavies stream 226 can be obtained from the bottom of the phenol finishing and drying column.

In the crude phenol unit 118, 218 phenol can be separated from non-phenol hydrocarbons, such as carbonyls, 2-MBF, and/or others (e.g. cumene, AMS, AMS dimers, DMBA, PCP, alkyl benzenes, and/or DCP) through distillation. The crude phenol unit 118, 218 can include a crude phenol column. In the crude phenol column the stream 120, 220 can be distilled to separate phenol from the non-phenol hydrocarbons. From the crude phenol column, phenol can be separated in to the first stream 101, 201. In some aspects, the distillation conditions in the crude phenol column can include a temperature of 120° C. to 180° C., or at least any one of, equal to any one of, or between any two of 120, 130, 140, 150, 160, 170 and 180° C., and/or a pressure of 0.3 bar to 0.6 bar, or at least any one of, equal to any one of, or between any two of 0.3, 0.35, 0.4, 0.45, 0.5, 0.55 and 0.6 bar. In some aspects, the first stream can be obtained from the top of the crude phenol column.

In the phenol treatment unit 222 residual carbonyls, 2-MBF, and/or other non-phenol hydrocarbons, or at least a portion of it left in the fourth stream 204, can be removed to obtain the processed fourth stream 224. In some aspects, phenol treatment unit 222 can include a distillation column. In the distillation column, the fourth stream 204 can be distilled by extractive distillation (e.g., hydroextraction) using water as azeotropic separation agent. In some aspects, the extractive distillation condition in the phenol treatment unit 222 can include a temperature of 70° C. to 180° C., or at least any one of, equal to any one of, or between any two of 70, 80, 90, 100, 110, 120, 130, 140, 150, 160, 170, and 180° C., and/or a pressure of 1 bar to 4 bar, or at least any one of, equal to any one of, or between any two of 1 and 2 bar. From the phenol treatment unit 222, phenol and water can be separated in to the stream 224.

The crude phenol stream 120, 220 can be obtained from a phenol production process. In some aspects, the phenol production process can be cumene oxidation based phenol production process. The cumene oxidation based phenol production process can include oxidation of cumene to produce phenol. Cumene can be obtained by a reaction between propylene and benzene, in excess, according to Friedel-Crafts mechanism. The reaction is exothermic and can use zeolite, phosphoric acid, or aluminum chloride catalyst. Cumene can be oxidized to form cumene hydroperoxide (CHP). CHP can be cleaved to form phenol and acetone. The crude phenol stream 120, 220 can contain phenol obtained in the cumene oxidation process. In some aspects, the crude phenol stream can contain 60 wt. % to 95 wt. %, or at least any one of, equal to any one of, or between any two of 60, 65, 70, 75, 80, 85, 90 and 95 wt. % of phenol. In some aspects, the crude phenol stream can further contain carbonyls, 2-MBF and others non-phenol hydrocarbons, such as cumene, AMS, AMS dimers, DMBA, PCP, alkyl benzenes, and/or DCP.

The first stream 101, 201 can contain 95 wt. % to 98 wt. %, or at least any one of, equal to any one of, or between any two of 95, 96, 97 and 98 wt. % of phenol. The first stream can further contain 0.1 wt. % to 1.5 wt. % of carbonyls, and 0.1 wt. % to 1 wt. % of 2-MBF. In some aspects, the first stream can further contain one or more of cumene, AMS, AMS dimers, DMBA, PCP, alkyl benzenes, and DCP. The carbonyls, 2-MBF, cumene, AMS, AMS dimers, DMBA, PCP, alkyl benzenes, and/or DCP in the first stream can be residuals after separation in the crude phenol column.

The second stream 102, 202 can contain 0.1 wt. % to 3 wt. %, or at least any one of, equal to any one of, or between any two of 0.1, 0.2, 0.3, 0.4, 0.5, 1, 1.5, 2, 2.5 and 3 wt. % of phenol and 97 wt. % to 99.9 wt. %, or at least any one of, equal to any one of, or between any two of 97, 97.5, 98, 98.5, 99, 99.5, 99.6, 99.7, 99.8 and 99.9 wt. % of water. The second stream can contain phenolic water from the BPA production process. In conventional BPA production process, phenolic water leaving a dehydration section of the process is sent to a solvent extraction unit, e.g. Glitsch unit, to recover phenol from the phenolic water. In certain aspects of the present invention, a portion of the phenolic water leaving the dehydration section, instead of being fed to the Glitsch unit, can form the second stream 102 and/or 202 (and/or also streams 228 and 208 in system 200). Optionally, in addition to or instead of the phenolic water leaving the dehydration section of BPA production process, the second stream 102, 202 can contain phenolic water from other units/sections of the BPA production process. The streams 228 and 208 can have same or similar composition as of the second stream 202, and can be sourced similarly, as of the second stream 202, from the BPA production process.

The fourth stream 104, 204 can contain phenol and water. Optionally the fourth stream can contain small amounts of residual non-phenol hydrocarbons from the third stream. The processed fourth stream 224 can contain phenol and water. Wt. % of non-phenol hydrocarbons, e.g., carbonyls and/or 2-MBF, in the processed fourth stream 224 can be lower compared to the fourth stream 204.

The fifth stream 105, 205 can contain 40 wt. % to 58 wt. %, or at least any one of, equal to any one of, or between any two of 40, 45, 50, 55, and 58 wt. % of phenol, and 35 wt. % to 55 wt. %, or at least any one of, equal to any one of, or between any two of 35, 40, 50 and 55 wt. % of water.

Figure 3:
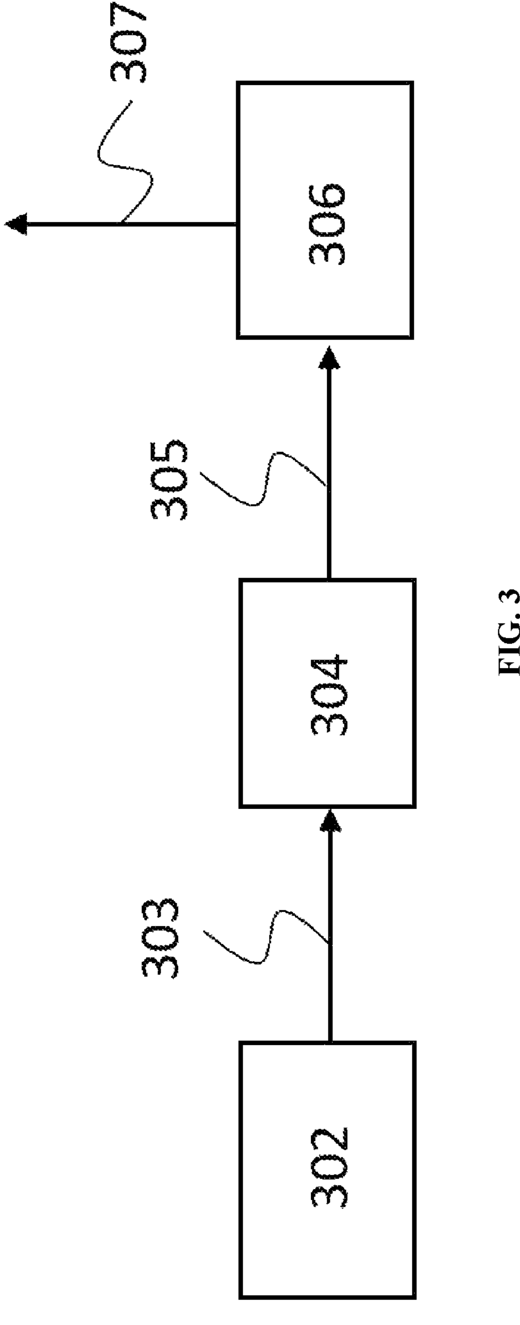
FIG. 3 is schematic of a BPA crystallization system of a BPA production process according to one embodiment of the present invention.

The fifth stream 105, 205 can contain mother liquor from a BPA crystallization unit of a BPA production process. Referring to FIG. 3, the BPA production process can include a BPA crystallization unit 302. In the BPA production process, the BPA produced can be crystallized in the BPA crystallization unit 302. Mother liquor 303 from the BPA crystallization unit 302 can be sent to a vacuum filter 304. From the vacuum filter 304 a vacuum filtered stream 305 containing phenol, water, and BPA can be sent to a water stripper column 306. A stream 307 containing phenol and water can leave from the top of the water stripper column 306. In certain aspects of the present invention, at least a portion of the stream 307, or the stream 307 can form the fifth stream 105, 205 and can be fed to the phenol finishing and drying unit 112, 212. Conventionally, in a BPA production process, the top stream (307, in FIG. 3) containing phenol and water from the water stripper column is sent to an azeotrope column to recover phenol. Since in certain aspects of the present invention, the stream 307 is processed in the phenol finishing and drying unit 112, 212, optionally the azeotrope column may not be used in the BPA production process.

The products stream 114, 214 can contain 98 wt. % to 99.998 wt. %, or 99 wt. % to 99.998 wt. %, or 98, 98.5, 99, 99.1, 99.2, 99.3, 99.5, 99.6, 99.7, 99.8, 99.9, 99.95, 99.99 and 99.998 wt. % of phenol. The products stream 114, 214 can contain i) less than 0.05 wt. %, or less than 0.04 wt. %, or less than 0.03 wt. %, or less than 0.02 wt. % of carbonyls and/or ii) less than 0.05 wt. %, or less than 0.04 wt. %, or less than 0.03 wt. %, or less than 0.02 wt. %, or less than 0.01 wt. % of 2-MBF.

Although embodiments of the present invention have been described with reference to blocks of FIGS. 1-3, it should be appreciated that operation of the present invention is not limited to the particular blocks and/or the particular order of the blocks illustrated in FIGS. 1-3. Accordingly, embodiments of the invention may provide functionality as described herein using various blocks in a sequence different than that of FIGS. 1-3.

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLES

Example 1

Method for Purifying Phenol

Simulations for phenol purification processes using ASPEN platform were perform. In a comparative example phenol was purified using a conventional process used to purify phenol in a phenol production process. In the conventional phenol purification process, FIG. 4, phenol was purified using a crude phenol column 406, a hydrocarbon removal and drying column 407, phenol treatment reactors 408, and a phenol finishing column 409. A stream 401 containing phenol from a phenol production process was purified in the crude phenol column 406. A phenol containing stream 402 from the crude phenol column 406, and a stream 403 containing water was fed to the hydrocarbon removal and drying column 407. In the hydrocarbon removal and drying column 407, carbonyls and 2-MBF were separated from phenol. A stream 404 containing carbonyls and 2-MBF was removed from the hydrocarbon removal and drying column 407. A stream containing phenol from the hydrocarbon removal and drying column 407, was further purified in the phenol treatment reactors 408 and the finishing column 409 to form a stream 405 containing purified phenol. In the inventive examples, examples A and B, phenol was purified according to the processes of FIGS. 1B and 2B, respectively. The flow rates and compositions of the streams in the comparative example, example A, and example B, are shown in Table 1, 2 and 3, respectively.

Phenol recovery for the comparative example, example A and example B, was 89.7%, 90% and 90% respectively. Phenol recovery was calculated as total phenol in the products stream divided by total phenol introduced in the process. Thus, processes of the present invention can result in higher phenol recovery compared to the convention purification process illustrated in FIG. 4. In inventive the examples A and B, phenolic water from respective BPA production processes, were used for hydroextraction in the hydrocarbon removal columns, wherein for the comparative process clean water was used in the hydrocarbon removal and drying column. Further in the examples A and B, in the phenol finishing and drying unit, the wet phenol in the mother liquor from the respective BPA crystallization unit, and the wet phenol from the respective hydrocarbon removal unit, was dried and purified together, reducing the overall equipment usage in the phenol purification methods of the phenol production process and the BPA production process. Thus, processes of the present invention can result in lesser energy use and lesser reliance on resources compared to the conventional purification process illustrated in FIG. 4.

TABLE 1

Figure 4:
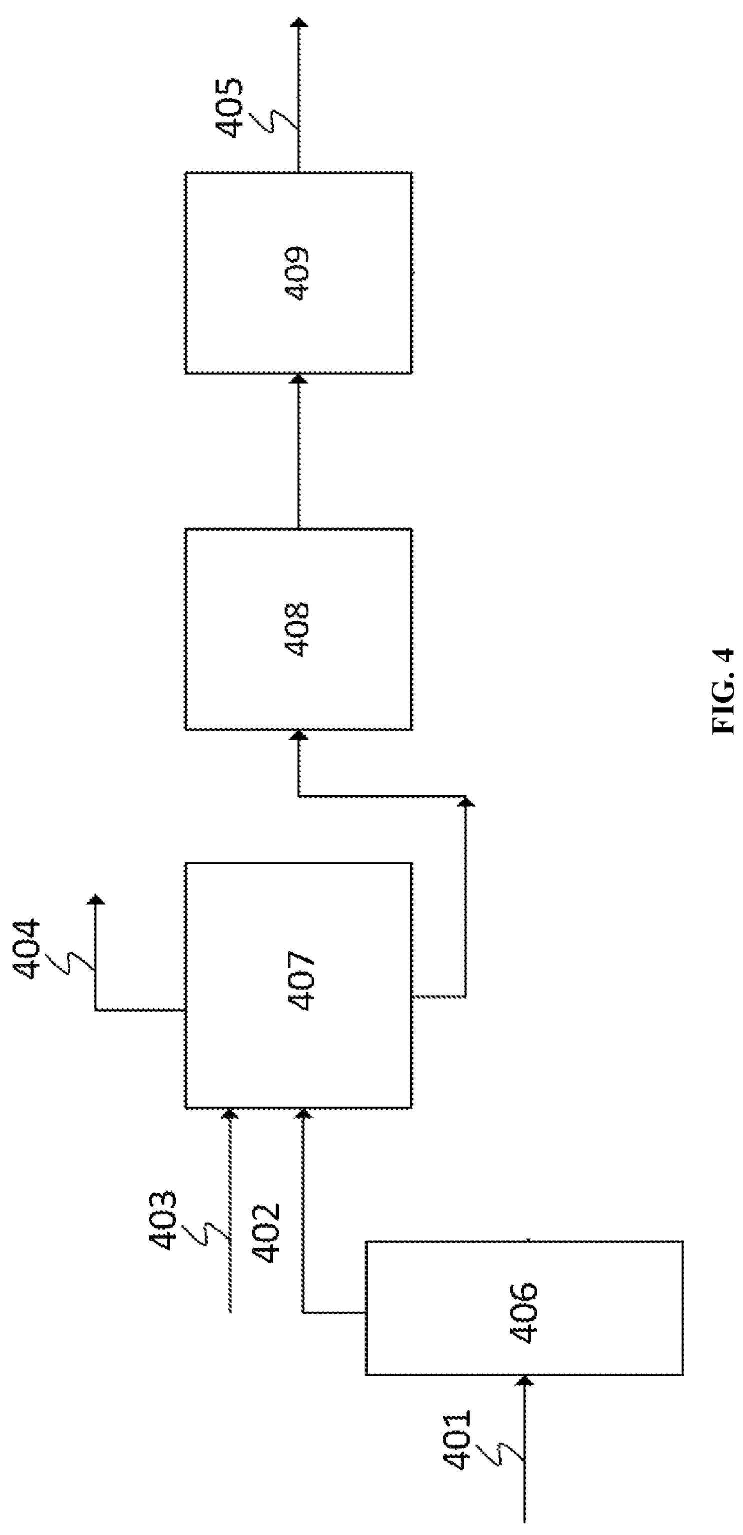
FIG. 4 is a schematic of a conventional phenol purification system according to a comparative example.

Flow rates and compositions of the streams for a conventional phenol purification process, comparative example (FIG. 4)

| | Stream 401 | Stream 402 | Stream 403 | Stream 404 | Stream 405 |
|---|---|---|---|---|---|
| Flowrate (kg/h) | 34019 | 30272 | 6674 | 7737 | 26671 |
| Phenol (wt %) | 87.55 | 96.48 | 0.00 | 7.16 | 99.99 |
| 2MBF (wt %) | 0.17 | 0.19 | 0.00 | 0.75 | 0.00 |
| Carbonyls (wt %) | 4.92 | 0.59 | 0.00 | 1.47 | 0.01 |
| Water (wt %) | 0.00 | 0.00 | 100.00 | 85.23 | 0.00 |
| Others (wt %) | 7.36 | 2.73 | 0.00 | 5.39 | 0.00 |

TABLE 2

Flow rates and compositions of the streams for example A (FIG. 1B)

| | Crude Phenol Stream | First Stream | Second Stream | Seventh Stream | Products Stream | Fifth Stream | Water Stream |
|---|---|---|---|---|---|---|---|
| Flowrate (kg/h) | 34019 | 29256 | 5020 | 6170 | 27758 | 1944 | 2209 |
| Phenol (wt %) | 87.55 | 96.44 | 0.13 | 10.01 | 99.90 | 51.87 | 37.25 |
| 2MBF (wt %) | 0.17 | 0.20 | 0.00 | 0.92 | 0.00 | 0.00 | 0.01 |
| Carbonyls (wt %) | 4.92 | 0.54 | 0.00 | 1.68 | 0.10 | 2.99 | 2.74 |
| Water (wt %) | 0.00 | 0.00 | 99.87 | 81.26 | 0.00 | 45.14 | 39.70 |
| Others (wt %) | 7.36 | 2.83 | 0.00 | 6.13 | 0.00 | 0.00 | 20.30 |

TABLE 3

Flow rates and compositions of the streams for example B (FIG. 2B)

| | Crude Phenol Stream | First Stream | Second Stream | Seventh Stream | Products Stream | Fifth Stream | Water Stream | Eight Stream |
|---|---|---|---|---|---|---|---|---|
| Flowrate (kg/h) | 34019 | 29248 | 4998 | 6164 | 27736 | 1944 | 6094 | 3888 |
| Phenol (wt %) | 87.55 | 96.38 | 0.13 | 9.81 | 99.94 | 51.87 | 13.80 | 0.13 |
| 2MBF (wt %) | 0.17 | 0.20 | 0.00 | 0.92 | 0.01 | 0.00 | 0.18 | 0.00 |
| Carbonyls (wt %) | 4.92 | 0.60 | 0.00 | 1.71 | 0.05 | 2.99 | 0.95 | 0.00 |
| Water (wt %) | 0.00 | 0.00 | 99.87 | 80.98 | 0.00 | 45.14 | 78.16 | 99.87 |
| Others (wt %) | 7.36 | 2.83 | 0.00 | 6.57 | 0.00 | 0.00 | 6.91 | 0.00 |

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method for purifying phenol, the method comprising:
- contacting a first stream comprising phenol with a second stream comprising wastewater from a bisphenol-A (BPA) production process to form a third stream;
- distilling the third stream to form a fourth stream comprising phenol and water;
- contacting the fourth stream with a fifth stream comprising mother liquor from a BPA crystallization unit of the BPA production process to form a sixth stream, wherein the fifth stream comprises 40 wt. % to 58 wt. % of phenol and 35 wt. % to 55 wt. % of water; and
- distilling the sixth stream to form a products stream comprising phenol.

2. The method of claim 1, wherein the first stream comprises 95 wt. % to 98 wt. % of phenol.

3. The method of claim 1, wherein the first stream is obtained from a cumene oxidation based phenol production process.

4. The method of claim 3, wherein an effluent from the cumene oxidation based phenol production process comprising 60 wt. % to 95 wt. % of phenol is separated in a crude phenol column to obtain the first stream.

5. The method of claim 1, wherein the first stream further comprises 0.1 wt. % to 1.5 wt. % of carbonyls and 0.1 wt. % to 1 wt. % of 2-methyl benzofuran (MBF).

6. The method of claim 1, wherein the second stream comprises phenolic water from the BPA production process.

7. The method of claim 1, wherein the second stream comprises 0.1 wt. % to 3 wt. % of phenol and 97 wt. % to 99.9 wt. % of water.

8. The method of claim 1, wherein distillation of the third stream comprises extractive distillation using water as azeotropic separation agent.

9. The method of claim 1, wherein the third stream is distilled in a hydrocarbon removal column at a temperature of 190° C. to 230° C. and/or a pressure of 1 bar to 3 bar.

10. The method of claim 5, wherein the distillation of the third stream separates at least a portion of the carbonyls and 2-MBF from phenol to form the fourth stream and a seventh stream comprising carbonyls and 2-MBF.

11. A method for purifying phenol, the method comprising:
- contacting a first stream comprising phenol with a second stream comprising wastewater from a bisphenol-A (BPA) production process to form a third stream;
- adding an acid to the third stream prior to distilling the third stream;
- distilling the third stream to form a fourth stream comprising phenol and water,
- contacting the fourth stream with a fifth stream comprising mother liquor from a BPA crystallization unit of the BPA production process to form a sixth stream; and
- distilling the sixth stream to form a products stream comprising phenol.

12. The method of claim 5, further comprising processing the fourth stream to remove at least a portion of residual carbonyls and 2-MBF from the fourth stream and produce a processed fourth stream, and then contacting the processed fourth stream with the fifth stream to form the sixth stream.

13. The method of claim 12, wherein the processing of the fourth stream comprises hydroextraction using water as an azeotropic separation agent.

14. The method of claim 1, further comprising contacting an eighth stream comprising phenolic water from the BPA production process with the fourth stream, the processed fourth stream, and/or the fifth stream.

15. The method of claim 14, wherein the eighth stream comprises 0.1 wt. % to 3 wt. % of phenol and 97 wt. % to 99.9 wt. % of water.

16. The method of claim 1, wherein the fifth stream is obtained from the BPA crystallization unit by a process comprising:
- vacuum filtering the mother liquor from the BPA crystallization unit to obtain a vacuum filtered stream comprising phenol, BPA, and water; and separating the vacuum filtered stream in a water stripper column to obtain the fifth stream comprising phenol and water as a top distillate from the water stripper column.

17. The method of claim 1, wherein the products stream comprises greater than 98 wt. % of phenol.

18. The method of claim 1, wherein the products stream comprises less than 0.05 wt. % of carbonyls and less than 0.01 wt. % of 2-MBF.

19. The method of claim 1, wherein the sixth stream is distilled at a phenol drying and finishing column at a temperature of 180° C. to 210° C. and/or a pressure of 0.5 bar to 2 bar.

* * * * *